United States Patent [19]

Mullins

[11] 4,017,544
[45] Apr. 12, 1977

[54] N-(NITROALKYL)-N'-PHENYL-p-PHENYLENEDIAMINES

[75] Inventor: Darrell Dexter Mullins, Norton, Ohio

[73] Assignee: Monsanto Company, St. Louis, Mo.

[22] Filed: Apr. 17, 1975

[21] Appl. No.: 569,119

Related U.S. Application Data

[62] Division of Ser. No. 435,676, Jan. 23, 1974, Pat. No. 3,896,162.

[52] U.S. Cl. .............................. 260/576; 260/485 S; 260/386 R; 260/571
[51] Int. Cl.² .................. C07C 87/64; C07C 93/14; C07C 69/54
[58] Field of Search .................. 260/576, 571, 576

[56] References Cited

UNITED STATES PATENTS

| 2,292,212 | 8/1942 | Dickey et al. ..................... 260/574 |
| 3,322,520 | 5/1967 | Brimer et al. ................. 260/576 X |

Primary Examiner—Daniel E. Wyman
Assistant Examiner—John J. Doll

[57] ABSTRACT

A method of inhibiting polymerization of unsaturated carboxylic acid esters and improved unsaturated carboxylic acid ester compositions are described. The method comprises, and the compositions are prepared by, incorporating into the ester composition a N-(nitroalkyl)phenylenediamine of the formula

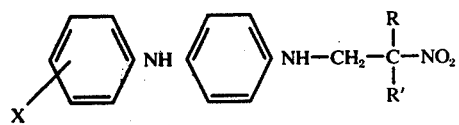

in which R is lower alkyl, R' is hydrogen, nitro or lower alkyl and X is hydrogen, lower alkyl or lower alkoxy.

2 Claims, No Drawings

N-(NITROALKYL)-N'-PHENYL-p-PHENYLENEDIAMINES

This is a division, of application Ser. No. 435,676, filed Jan. 23, 1974, now U.S. Pat. No. 3,896,162.

BACKGROUND OF THE INVENTION

This invention relates to methods of inhibiting polymerization of unsaturated monomers, more particularly it relates to methods of inhibiting polymerization of unsaturated carboxylic acid esters and to improved unsaturated carboxylic acid ester compositions. Processes concerning the preparation and the stabilization of unsaturated carboxylic esters are found in Patent Office Class 260, subclass 486.

Substantial quantities of unsaturated carboxylic acid esters, for example methyl methacrylate, are manufactured for use as intermediates in the production of polymers and copolymers. During manufacture, transportation and storage of these esters, it is essential that polymerization of these monomers is avoided. If premature polymerization occurs during manufacture, the polymer fouls or completely plugs production equipment and transfer lines which fouling leads to expensive dismantling and cleaning of production facilities. The problem is particularly acute during the distillation step which step is required to isolate the desired ester monomer. If premature polymerization occurs during transportation or storage, recovery of the polymer from the storage vessel is extremely difficult. Of course, any time that premature polymerization occurs, the yield of the desired monomer is reduced. It is common practice to add stabilizers to unsaturated esters to assure inhibition of polymerization. Preferred polymerization inhibitors not only prevent premature polymerization they do not unduly interfere with the desired polymerization reaction or affect the polymer properties in any way. In polymer production, the effect of polymerization inhibitors is generally reduced by addition of polymerization initiators. Known polymerization inhibitors include phenols (hydroquinone being commonly used) and aliphatic and aromatic amines, for example, phenylenediamines. The subject invention concerns an improved class of phenylenediamine inhibitors.

SUMMARY OF THE INVENTION

A class of N-(nitroalkyl)-N'-phenyl-p-phenylenediamines has been found which possesses enhanced activity in respect to inhibiting the polymerization of unsaturated carboxylic acid esters. The inhibitors of this invention are characterized by the formula

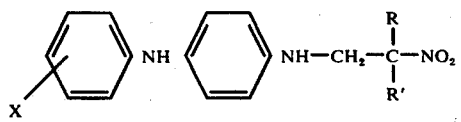

in which R is lower alkyl, R' is hydrogen, nitro or lower alkyl and X is hydrogen, lower alkyl or lower alkoxy. Inhibitors in which R and R' are lower alkyl and X is hydrogen comprise a preferred subclass. The presence of a nitro group in the beta position of the alkyl radical attached to nitrogen of the phenylenediamine enhances the inhibitor activity. The presence of lower alkyl or lower alkoxy radicals on the phenyl radical has essentially no effect upon inhibitor activity and unsubstituted compounds (X is hydrogen) are preferred.

The terms used herein and in the claims mean as follows: "Lower alkyl" means an alkyl radical derived from removal of one hydrogen atom from alkane of 1-5 carbon atoms. Straight chain unbranched radicals are preferred. Illustrative examples of satisfactory lower alkyl radicals are methyl, ethyl, propyl, isopropyl, n-butyl, isobutyl, sec-butyl, tert-butyl, pentyl and isopentyl with methyl being the preferred radical. Alkoxy comprises an alkyl radical attached to the remainder of the molecule by oxygen.

The term "unsaturated carboxylic acid esters" is used in the generic sense and means aliphatic esters of unsaturated mono-, di-, and tricarboxylic acids. Lower alkyl esters of ethylenically unsaturated monocarboxylic acids are preferred. The size of the carboxylic acid or ester moiety is immaterial. Polymerization of esters of unsaturated carboxylic acids of 30 carbon atoms or more are inhibited with the inhibitors of this invention. Illustrative examples of compounds stabilized with the inhibitors of this invention are the methyl, ethyl, butyl, and 2-ethylhexyl esters of the following acids: acrylic methacrylic, angelic, crotonic, isocrotonic, propynoic, sorbic, oleic, elaidic, linoleic, $\alpha$-eleostearic, $\beta$-eleostearic, $\alpha$-linolenic and erucic. Other examples are the dimethyl, diethyl, dibutyl, and di(2-ethylhexyl) esters of maleic acid, fumaric acid, itaconic acid and acetylenedicarboxylic acid, and trialkyl esters of aconitic-(1,2,3-propenetricarboxylic) acid. A preferred subgroup of unsaturated carboxylic acid esters are acrylate esters derived from acrylic and methacrylic acids. These esters are characterized by the formula $CH_2=C(R_2)C(O)OR_3$ in which $R_2$ is hydrogen or methyl and $R_3$ is alkyl of 1-8 carbon atoms. Lower alkyl esters are preferred.

The inhibitors of this invention are prepared by known procedures. For example, N-(2-nitroalkyl)-N'-phenyl-p-phenylenediamines may be prepared by reacting a nitroalkane and 4-amino-diphenylamine with formaldehyde or by reacting a 2-nitro alcohol with 4-aminodiphenylamine.

Illustrative inhibitors of the invention are:
N-(2-methyl-2-nitrobutyl)-N'-phenyl-p-phenylenediamine
N-(2-methyl-2-nitropentyl)-N'-phenyl-p-phenylenediamine
N-(2-ethyl-2-nitrobutyl)-N'-phenyl-p-phenylenediamine
N-(2,3,3-trimethyl-2-nitrobutyl)-N'-phenyl-p-phenylenediamine
N-(2-ethyl-2-nitropentyl)-N'-phenyl-p-phenylenediamine
N-(2-propyl-2-nitropentyl)-N'-phenyl-p-phenylenediamine
N-(2-propyl-2-nitrohexyl)-N'-phenyl-p-phenylenediamine
N-(2-isopropyl-3,3-dimethyl-2-nitrobutyl)-N'-phenyl-p-phenylenediamine
N-(2,2-dinitro-propyl)-N'-phenyl-p-phenylenediamine
N-(2,2-dinitro-butyl)-N'-phenyl-p-phenylenediamine
N-(2-methyl-2-nitropropyl)-N'-(4-methoxyphenyl)-p-phenylene-diamine The inhibitors are incorporated into unsaturated carboxylic acid ester compositions by simple addition. Normally, the inhibitor is added to the reactor after the ester is prepared but prior to distilling the reaction mixture to isolate the unsaturated ester from by-products and reaction media. Generally, additional quantities of inhibitor are added to the ester fraction recovered after distillation to inhibit polymerization during storage. Although the effect of the inhibitors are discussed in terms of inhibiting polymerization, it is probably more accurate to think of the inhibition effect as extending the induction period prior to the onset of polymerization rather than affecting polymerization rate. Regardless of the mode of operation, the consequence of the inhibitor addition is a more stable unsaturated carboxylic acid ester monomer composition which remains in monomer form longer than a similar ester composition without inhibitor added.

The inhibitor effect is concentration dependent, i.e., the more inhibitor added the longer the time period before the onset of polymerization. The N-phenyl-p-phenylenediamine inhibitors of this invention are particularly potent. Quantities of one part per million by weight or less based upon the weight of ester are sufficient to inhibit polymerization. Normally, 5–50 parts per million are recommended for most applications with amounts of 50–200 parts per million being used sometimes and 200–5000 parts per million being used where more severe conditions are encountered which require greater inhibition. Although even larger quantities are effective, higher dosages are usually unnecessary and are avoided for reason of economy. The amount required for any desired induction time may be readily determined by the methods hereinafter described.

The "onset time ", the time from the beginning of the test until polymerization begins, may be conveniently determined either by measuring the temperature of a sample to detect the liberation of heat which takes place when polymerization begins or by measuring the change in volume of a sample to detect the volume reduction which takes place as polymerization proceeds. Either method is applicable to uncatalyzed samples or samples to which polymerization initiator is added. The exothermic method is described by Bockstahler, et al., *Ind. & Eng. Chem.*, 50 (10), 1581. The dilatometric method is described by Caldwell and Ihrig, *J. Am. Chem. Soc.*, 84, 2886.

The inhibitors of this invention are evaluated by the exothermic method essentially as described by Bockstahler, et al., supra. The time required for a test monomer to begin to polymerize is determined at elevated temperature. The test is based on the principle that polymerization is exothermic so that initiation is detected by observing temperature change between a test sample and a stable reference sample maintained in the same environment. The procedure comprises placing a test tube (adapted to accommodate a thermocouple) containing a measured amount of monomer in a constant temperature bath (maintained within ± 0.25° C). A similar test tube containing silicone oil is used as a reference sample. A differential thermocouple continuously measures the difference in the temperature ΔT between the test and reference samples. All samples are measured in the dark to eliminate any effects due to light. The thermocouple output is recorded on a strip recorder thereby providing a record of ΔT versus time. When polymerization occurs a sharp deflection in ΔT is observed from which the onset time is determined.

DESCRIPTION OF PREFERRED EMBODIMENTS

Satisfactory procedures for preparing the inhibitors of the invention are illustrated below:

A solution of 2-methyl-2-nitro-1-propanol, 119.1 grams (1.0 mole), in 300 ml of ethanol is added dropwise over a period of three hours to a stirred refluxing solution of 4-amino-diphenylamine, 184 grams (1.0 mole), and potassium hydroxide 4 grams, in 200 ml of ethanol. The mixture is stirred at reflux for 24 additional hours. After cooling to 0° C, the precipitate is recovered by filtration and air-dried. N-(2-methyl-2-nitropropyl)-N'-phenyl-p-phenylenediamine is recovered, 237 grams (83% yield), which after recrystallization from alcohol melts at 127°–128° C.

Ethylmethacrylate is the test monomer used to illustrate the effect of the inhibitors of the invention. A supply of ethylmethacrylate containing hydroquinone inhibitor is repeatedly washed with 0.5 N sodium hydroxide solution and finally with water to remove all hydroquinone inhibitor from the material. Fifty grams of the unstabilized ethylmethacrylate is added to an above described test tube. A solution of inhibitor is prepared by adding a carefully weighed quantity of a N-(2-nitroalkyl)-N'-phenyl-p-phenylenediamine inhibitor to 10 ml of unstabilized ethylmethacrylate. The appropriate volume of inhibitor solution is then added to the test sample with a micropipette to give an inhibitor concentration of 5 parts per million. The test is placed in a constant temperature bath at 85° C and the onset time is determined as previously described. The onset time is recorded in hours. When the test is repeated, the average onset time is reported. The results are shown in Table I. Sample I is a control consisting of ethylmethacrylate with no inhibitor present. Sample 2 contains a N-(alkyl)-N'-phenyl-p-phenylenediamine inhibitor. Sample 3 illustrates an inhibitor of the invention.

TABLE I

| Sample | Inhibitor (5 ppm) | Onset Time, hrs. |
|---|---|---|
| 1 | None | 7 |
| 2 | N-isobutyl-N'-phenyl-p-phenylenediamine | 82 |
| 3 | N-(2-methyl-2-nitropropyl)-N'-phenyl-p-phenylenediamine | 119 |

The data demonstrate that the presence of the nitro group enhances the inhibiting activity of the p-phenylenediamine inhibitor.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. A compound of the formula

in which R and R' are independently lower alkyl.

2. The compound of claim 1 in which R and R' are methyl.

* * * * *